United States Patent [19]

Wittwer et al.

[11] Patent Number: 4,673,438
[45] Date of Patent: Jun. 16, 1987

[54] POLYMER COMPOSITION FOR INJECTION MOLDING

[75] Inventors: Fritz Wittwer, Lupsingen; Ivan Tomka, Bourguillon, both of Switzerland

[73] Assignee: Warner-Lambert Company, Morris Plains, N.J.

[21] Appl. No.: 796,517

[22] Filed: Nov. 8, 1985

Related U.S. Application Data

[63] Continuation of Ser. No. 579,318, Feb. 13, 1984, abandoned, which is a continuation-in-part of Ser. No. 467,982, Feb. 18, 1983, abandoned.

[51] Int. Cl.$^4$ .................. C09H 11/00; C08L 3/00; B28B 7/20
[52] U.S. Cl. .................. 106/126; 106/128; 106/130; 106/213; 264/328.1; 264/328.18; 424/473
[58] Field of Search .................. 264/328.1, 38.18, 330; 106/126, 128, 130, 213; 424/14, 19

[56] References Cited

U.S. PATENT DOCUMENTS

| | | | |
|---|---|---|---|
| 2,602,755 | 7/1952 | Silvernail | 106/189 |
| 3,117,014 | 1/1964 | Klug | 106/213 |
| 3,137,592 | 6/1964 | Prutzman et al. | 127/32 |
| 3,911,159 | 10/1975 | Heusdens | 426/580 |
| 3,954,104 | 5/1976 | Kraskin et al. | 128/263 |
| 4,076,846 | 2/1978 | Nakatsuka | 426/89 |
| 4,138,013 | 2/1979 | Okajima | 206/528 |
| 4,216,240 | 8/1980 | Shirai et al. | 426/512 |
| 4,232,047 | 11/1980 | Sair et al. | 426/96 |
| 4,415,593 | 11/1983 | Glass et al. | 426/4 |

FOREIGN PATENT DOCUMENTS 2001533  7/1971  Fed. Rep. of Germany ...... 264/186
  19645  6/1978  Japan .

Primary Examiner—Theodore Morris
Attorney, Agent, or Firm—Howard Olevsky; Stephen Raines

[57] ABSTRACT

Capsules and other shaped products formed from a moldable starch composition in an injection molding device is disclosed in the present invention. The composition comprising starch having a molecular mass range of 10,000 to 20,000,000 Dalton, and a water content range from 5 to 30% by weight. The starch contains about 0 to 100% of amylose, and about 100 to 0% of amylo-pectin.

24 Claims, 9 Drawing Figures

POLYMER COMPOSITION FOR INJECTION MOLDING

This is a continuation of application Ser. No. 579,318 filed on Feb. 13, 1984 which is a continuation-in-part of Ser. No. 467,982 filed Feb. 18, 1983, now both abandoned.

BACKGROUND OF THE INVENTION

A. Field of the Invention

The present invention relates to a moldable starch composition for use in an injection molding device to produce capsules. The present invention utilizes starch made from corn wheat, potatoes, rice, tapioca and the like. Said types of starch have a usual molecular mass range of 10,000 to 20,000,000 Dalton.

The starch contains about 0 to 100% of amylose, and about 100 to 0% of amylo-pectin; preferably 0 to 70% of amylose, and about 95 to 10% of amylo-pectin and most preferably potato starch and maize starch.

Hydrophilic polymers are polymers with molecular masses from approximately $10^3$ to $10^7$ Dalton carrying molecular groups in their backbone and/or in their side chains and capable of forming and/or participating in hydrogen bridges. Such hydrophilic polymers exhibit in their water adsorption isotherm (in the temperature range between approximately 0 to 200 degrees C.) and inflection point close to the water activity point at 0.5.

Hydrophilic polymers are distinguished from the group called hydrocolloids by their molecular dispersity of said hydrophilic polymers a fraction of water—according to the working range of the present invention—of 5 to 30% by weight of said hydrophilic polymers must be included provided that the temperature of said hydrophilic polymers is in the working range between 80 degrees C. and 240 degrees C. of the present invention.

It is a primary object of the present invention to utilize starch compositions in the production of injection molded products, especially capsules.

REFERENCES TO COPENDING PATENT APPLICATIONS

Concurrently with this application please also refer to patent application U.S. Ser. No. 372,599 filed 4-28-82, now U.S. Pat. No. 4,415,593, to patent application U.S. Ser. No. 362,177 filed 3-26-82, and to patent application U.S. Ser. No. 362,430 filed 3-26-82, now abandoned, all of which are copending with this application.

B. Description of the Prior Art

Capsule-making machines have been developed to utilize dip-molding technology. Such technology involves the dipping of capsule-shaped pins into a gelatin solution, removing the pins from the solution, drying of the gelatin upon the pins, stripping off the gelatin capsule parts from the pins, adjusting for length, cutting, joining and ejecting the capsules. Prior art capsule-making machines have utilized the combination of mechanical and pneumatic elements to perform these functions at speeds up to about 1,200 size 0 capsules per minute. While the above described apparatusses are in general suitable for the intended purposes, it is desirable to produce capsules by injection molding at considerably higher speed, while at the same time precisely controlling the properties of the starch in order to produce the capsules hygienically and with minimum dimensional deviations so that the capsules can be filled on high speed equipment.

A prerequisite for any material to be moldable by an injection process is its ability to pass a glass transition point at a temperature compatible with the thermal stability of the material and the technical possibilities of an injection molding device. A pre-requisite of any material to deliver shaped products of high dimensional stability in an injection molding process is its minimum elastic recovery after the mold is opened. This can be achieved by setting the dispersity of said material at the molecular level during the injection process.

Shirai et al. in U.S. Pat. No. 4,216,240 describes an injection molding process to produce an oriented fibrous protein product. The fibrous product obtained by this process differs fundamentally from the transparent glasslike material of the capsules obtained from the present invention. Furthermore to obtain a flowable mass for the molding process, the protein mixtures used by Shirai et al. have to be denatured and thus lose their capacity to undergo dissolution.

Nakatsuka et al. in U.S. Pat. No. 4,076,846 uses binary mixtures of starch with salts of protein materials to obtain an edible shaped article by an injection molding process. With the present invention shaped articles can be produced with starch without admixture with salts of protein materials therewith.

Heusdens et al. in U.S. Pat. No. 3,911,159 discloses the formation of filamentous protein structures to obtain edible products of improved tenderness. With the present invention shaped articles are produced without a filamentous protein structure.

The use of an injection molding device for producing capsules with starch is new and has not been suggested in the technical literature. Many useful products can be prepared by the injection molding of starch other than capsules with the necessity of high form stability and minimum dimensional deviations. These products would include candies, packaging containers for foodstuffs, pharmaceuticals, chemicals, dyestuffs, spices, fertilizing combinations, seeds, cosmetics and agricultural products and matrices of various shapes and size of starch compositions containing substances and/or active ingredients including food stuffs, pharmaceuticals, chemicals, dyestuffs, spices, fertilizing combinations, seeds, cosmetics and agricultural products, which are microdispersed within the matrix and released from it through disintegration and/or dissolution and/or bioerrosion and/or diffusion depending on the solubility characteristics of the used starch composition. Some of these products may also result in a controlled release delivery system for the enclosed substance. Furthermore, medical and surgery products can be prepared by injection molding starch compositions. The biodegradable nature of starch makes it environmentally desirable over certain materials presently being used. In addition, the non-toxic mixture of the materials further enhances their desirability as a material to be used in the injection molding industry. It is an object of this invention to encompass all injection moled products that may be produced by the teachings of that invention. The present invention distinguishes from the known prior art described above, by the recognition that starch possesses a dissolution point within a temperature range usable for an injection molding process, provided the water content of the starch lies within a characteristic range, giving allowance to avoid any essential drying or humidification processes of the capsules. Above the dissolution point the starch is in the state of molecular dispersity. Due to the present invention the starch during the injection molding process is for a considerable time at a temperature which is higher than the temperature of the dissolution point. When materials, such as medicaments, food-stuffs, etc. are dispersed in the starch compositions, quantities can not be employed that will so effect the properties of the starch that it will no longer be injection moldable.

SUMMARY OF THE INVENTION

The present invention covers an improved starch composition for use in an improved automatic injection molding device to control the optimum time, temperature pressure and water content of the composition is formed and shaped parts and object molded from said composition. The starch has a molecular mass range of 10,000 to 20,000,000 Dalton.

The starch composition has a water content range of approximately 5 to 30% by weight.

The starch contains about 0 to 100% of amylose, and about 100 to 0% of amylo-pectin.

It is therefore a primary object of the present invention to provide a new and improved moldable composition of starch for use with an injection molding apparatus which alleviates one or more of the above described disadvantages of the prior art compositions.

It is a further object of the present invention to provide an improved moldable composition of starch for use with an injection molding apparatus in a method of molding capsules at high speed and with precision in order to use the capsules with high speed filling equipment.

It is a still further object of this invention to provide useful injection molded products, especially capsules, and a process for preparing said injection molded products.

BRIEF DESCRIPTION OF THE DRAWINGS

The invention both as to its organization and method of operation together with further objects and advantages thereof will best be understood by reference to the following specifications and taken in conjunction with the accompanying drawings.

DETAILED DESCRIPTION OF THE PREFERRED EMBODIMENT

Figure 1:
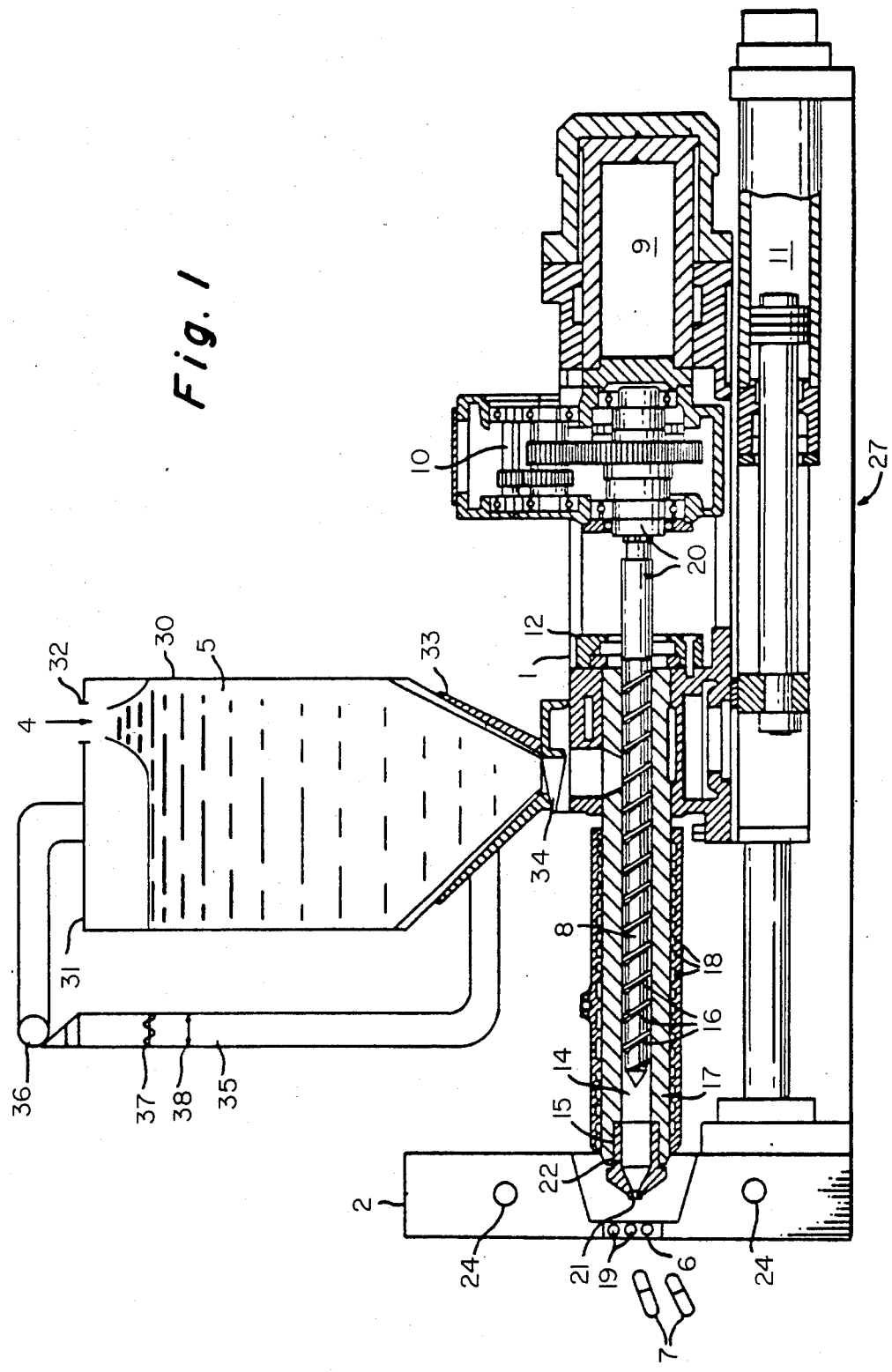
FIG. 1 is a schematic layout of a reciprocating screw injection molding device for making capsule parts.

Referring now to FIG. 1 the injection molding device 27 generally consists of three units: a hopper unit 5, an injection unit 1 and a molding unit 2.

The function of the hopper unit 5 is receiving, storing, maintaining and feeding starch 4 at a constant temperature and at a constant water content. The hopper unit 5 comprises a vertical cylinder 30 having a closed top 31 with an inlet 32 therein to receive starch 4. At the bottom of the vertical cylinder 30 is a closed conical funnel 33 and a discharge outlet 34 to feed starch 4 into an inlet 34 of the injection unit 1. There is an air duct 35 communicating between the closed top 31 and the conical funnel 33 wherein air is circulated by a blower 36, the air temperature is maintained by a thyristor 37 and the air relative humidity is maintained by a steam injector 38.

The function of the injection unit 1 is melting, dissolving in water, and plasticizing in the extruder barrel 17 the starch 4 fed from the hopper unit 5 into the extruder inlet 54 and injecting the plasticized starch 14 into the molding unit 2.

The function of the molding unit 2 is automatically holding, opening and closing the mold 6 having capsule shaped cavities 19 therein, and ejecting the capsule parts 7 therefrom.

Within the injection unit 1 the screw 8 both rotates and undergoes axial reciprocal motion. When the screw 8 rotates, it performs the functions of melting, dissolving in water, and plasticizing the starch 4. When the screw 8 moves axially, it performs the function of injecting by transporting and ramming the plasticized starch 14 into the mold 6. The screw 8 is rotated by a variable-speed hydraulic motor 9 and drive 10, and its axial motion is reciprocated by a duplex hydraulic cylinder 11.

Compression of the plasticized starch 14 in front of the rotating screw 8 forces back the screw assembly 20 containing the screw 8, the drive 10 and the motor 9. When the screw assemby 20 reaches a preset back position a limit switch 12 is contacted. When a defined time has elapsed during which the starch 4 becomes fully plasticized starch 14 the hydraulic cylinder 11 brings the screw assembly 20 forward and uses the screw 8 as a ram for the plasticized starch 14 to be injected through a valve body assembly 50 including a one-way valve 15, a needle valve 23, nozzle 22 and an outlet port 21 into the molding unit 2. The one-way valve 15 prevents the plasticized starch 14 from going back over the helical flutes 16 of the screw 8. The extruder barrel 17 has heating coils 18 to heat the starch 4 while it is being compressed by the screw 8 into plasticized starch 14. It is desirable for the plasticized starch 14 to be heated at the lowest possible temperature and to be transported with the lowest possible speed of the screw 8. The speed of the screw 8 and the heating of the plasticized starch 14 within the extruder barrel 17 by the steam heating coils 18 control the quality and the output rate of the plasticized starch 14 injected into the molding unit 2. The molding unit 2 holds the mold 6 having capsule shaped cavities 19 into which the plasticized starch 14 is injected and maintained under pressure. Refrigerant cooling conduits 24 encircle the mold 6 so that when the plasticized starch 14 in the mold 6 has cooled and sufficiently solidified, the molding unit 2 opens, the mold 6 separates and the capsule parts 7 are ejected.

Figure 2:
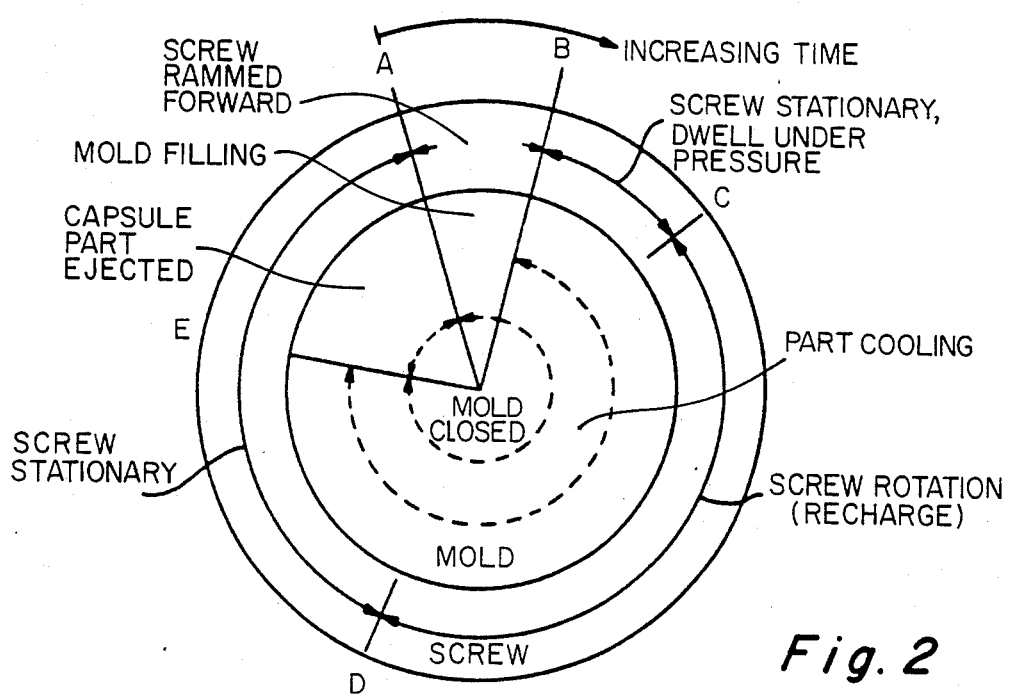
FIG. 2 is a schematic of an injection molding work cycle for making capsule parts.

Referring now to FIG. 1 and also to FIG. 2 which depicts the injection molding work cycle for starch 4 containing approximately 20% water, by weight. In general the work cycle of starch 4 is as follows in the injection molding device 27 of the present invention:

a. starch 4 is fed into the hopper unit 5 where it is received, stored and maintained under conditions of temperature ranging from ambient to 100° C., pressure ranging from $1-5 \times 10^5$ Newtons per square meter ($N \times m^{-2}$) and water content ranging from 5 to 30% by weight of starch b. the stored starch 4 is melted under controlled condition of temperature ranging from 80° to 240° C., water content ranging from 5 to 30% by weight of starch and pressure ranging from 600 to $3000 \times 10^5 N \times m^{-2}$, c. the molten starch 4 is dissolved in water under controlled conditions of temperature ranging from 80° to 240° C. pressures ranging from 600 to $3000 \times 10^5 N \times m^{-2}$ and water content ranging from 5 to 30% by weight of starch.

d. the dissolved starch 4 is plasticized under controlled conditions of temperature ranging from 80° to 240° C., pressure ranging from 600 to $3000 \times 10^5 N \times m^{-2}$ and water content ranging from 5 to 30% by weight of starch.

e. the plasticized starch 14 is injected into the mold 6 under controlled conditions of temperature above 80° C., injection pressure ranging from 600 to $3000 \times 10^5 N \times m^{-2}$ and a clamping force of the mold 6 with a range of approximately 100 to 10,000 Kilo Newton, and f. the capsule-shaped parts 7 are ejected from the plasticized starch 14 within the mold 6.

Beginning at point A of FIG. 2 the screw 8 moves forward and fills the mold 6 with plasticized starch 14 until Point B and maintains the injected plasticized starch 14 under high pressure, during what is called the hold time from point B until Point C of FIG. 2. At Point A the one-way valve 15 at the end of the screw 8 prevents the plasticized starch 14 from flowing back from the cylindrical space in front of the screw 8 into the helical flutes of screw 8. During hold time, additional plasticized starch 14 is injected, offsetting contraction due to cooling and solidification of the plasticized starch 14. Later, the outlet port 21, which is a narrow entrance to the molding unit 2 closes, thus isolating the molding unit 2 from the injection unit 1. The platicized starch 14 within the mold 6 is still at high pressure. As the plasticized starch 14 cools and solidifies, pressure drops to a level that is high enough to ensure the absence of sinkmarks, but not so high that it becomes difficult to remove the capsule parts 7 from the capsule-shaped cavities 19 within the mold 6. After the outlet port 21 closes, at Point C, screw 8 rotation commences. The plasticized starch 14 is accommodated in the increased cylindrical space in front of the screw 8 created by its backward axial motion until Point D. The flow rate of the plasticized starch 14 is controlled by the speed of the screw 8 and the pressure is controlled by the back pressure (i.e., the hydraulic pressure exerted on the screw assembly 20) which in turn determines the pressure in the plasticized starch 14 in front of the screw 8. After plasticized starch 14 generation for the next shot into the mold 6, the screw 8 rotation ceases at Point D. The starch 4 on the stationary screw 8 is held at melt temperature from Points D to E by heat conduction from the heating coils 18 on the extruder barrel 17. Meanwhile, the solidified capsule parts 7 are ejected from the mold 6. Thereafter, the mold 6 closes to accept the next shot of plasticized starch 14. All of these operations are automated and controlled by a microprocessor as hereinafter described.

Figure 3:
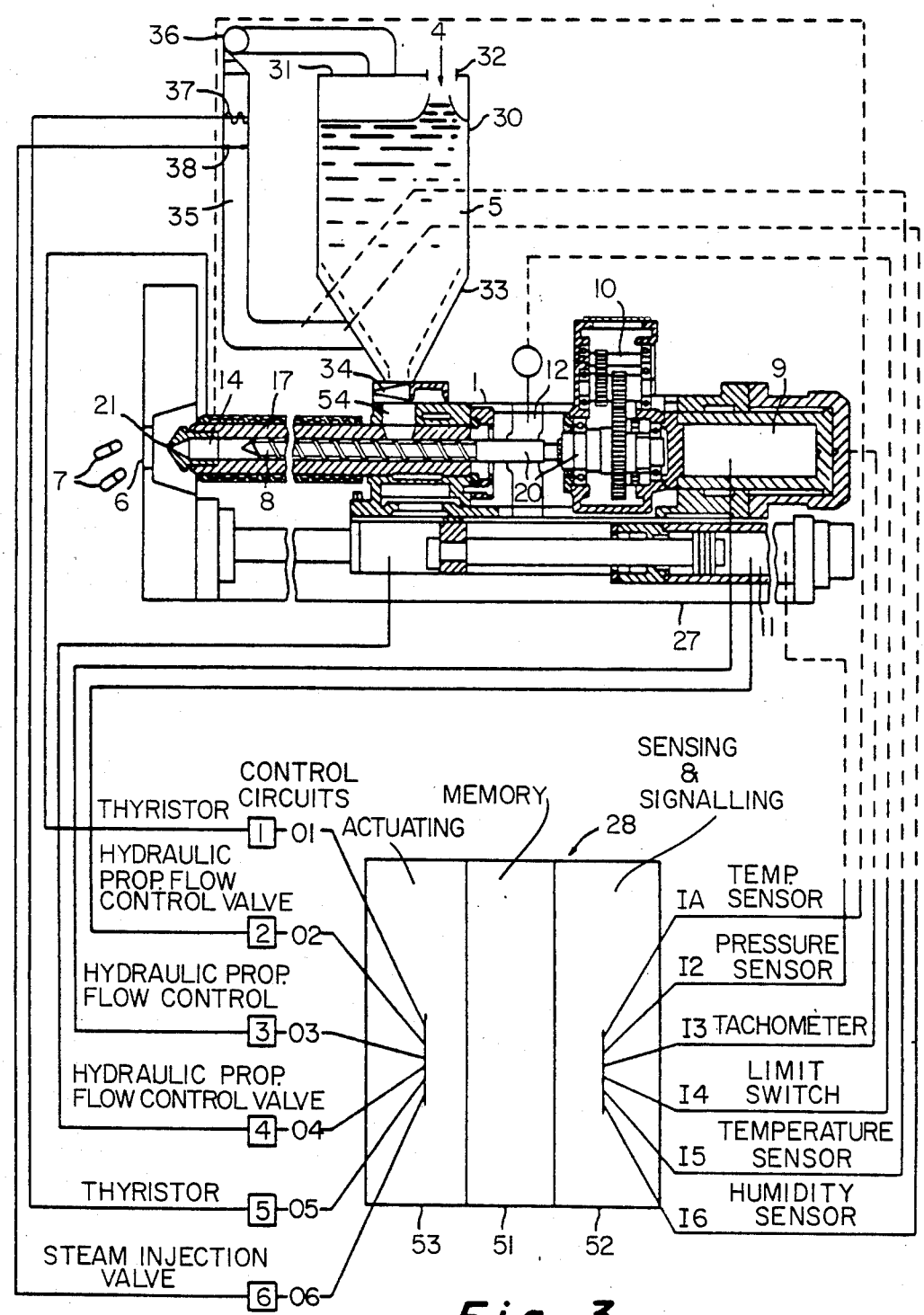
FIG. 3 is a schematic of an embodiment of a combined injection molding device-microprocessor apparatus for capsule parts.

Referring now to FIG. 2 and and also to FIG. 3. The injection molding work cycle of FIG. 2 is accomplished on the injection molding device 27 of FIG. 3 by hydraulic and electrical components and the corresponding circuits controlled by the microprocessor 28 of FIG. 3.

Through the use of solid-state circuitry and of speed, temperature, limit and pressure switches for the electric and hydraulic systems, the microprocessor 28 of the present invention utilized command signals in its memory 51 for the parameters of time, temperature and pressure conditions of Table 1 below for the injection molding work cycle of FIG. 2 to be accomplished by the injection molding device of FIG. 3 for producing capsule parts 7.

TABLE 1

Ranges of Time, Temperature and Pressure at the top of the Screw for the Injection Molding Work Cycle of FIG. 2:

| | POINTS | | | | |
|---|---|---|---|---|---|
| | A | B | C | D | E |
| | −2 | −2 | −2 | −2 | −2 |
| Time (seconds) | 10 −1 | 10−1 | 10−1 | 10−1 | 10−1 |
| Temperature (°Celsius) | ambient−100 | 80-240 | 80-190 | 80-240 | 80-240 |
| Pressure ($10^5 \times N \times m^{-2}$) (Newtons per square meter) | | A-B 600-3000 | B-C 600-3000 | C-D 10-1000 | D-E 10-1000 |

Referring now to FIG. 3 illustrating the combined injection molding device 27 and microprocessor 28 utilizing the method of present invention.

The combined injection molding device 27 and microprocessor 28 comprises six control circuits of which five are closed-loop, fully analog, and one is on-off. Starting at molding cycle Point A in FIG. 2, the injection molding work cycle operates as follows:

When sufficient plasticized starch 14 has accumulated in front of the screw 8 (microprocessor limit switch controlled) and also when the screw assembly 20 carrying the screw 8, drive 9 and hydraulic motor 11 has been pushed far enough backwards against a constant back-pressure as controlled by control circuit 2, limit switch 12 will be actuated by position sensing circuit I4. The two conditions for actuating cylinder 11 (barrel unit forward) are: (1) clamping force of the mold is built-up, and (2) limit switch 12 is activated. This rams the barrel 17 together with the nozzle 14 with screw assembly 20 forward, thus for sealing purposes. Sufficient pressure is controlled by control circuit 2 with means of pressure sensor $I_2$. Under these conditions hydraulic piston 9 rams the screw assembly 20 forward, thus injecting the plasticized starch 14 into the mold 6 when molding cycle Point B of FIG. 2 is reached, and, as controlled by the microprocessor 28, the screw 8 remains for a certain period of time until Point C stationary in this forward position under high pressure.

From molding cycle Point B of FIG. 2 onwards the plasticized starch 14 cools down in the mold 6 and the port 21 closes at molding cycle Point C of FIG. 2.

At molding cycle Point C of FIG. 2 the screw 8 starts to rotate again and the hydraulic pressure reduces from holding pressure to back pressure in the hydraulic cylinder 11. This pressure set is less than the holding pressure at Point C.

The barrel 17 is kept under constant pressure towards the mold 6 by the pressure in the back position of the hydraulic cylinder 11. This is achieved by means of the control circuit 2 where a proportional hydraulic valve is controlled by a pressure sensor circuit $I_2$.

As the screw 8 rotates a recharge of starch 4 is made from the hopper 5. During a certain time period and at a defined rotating speed of the screw 8, controlled by control circuit 3, a precise amount of starch 4 is fed into the extruder barrel 17. Control circuit 3 is actuated by speed sensor circuit $I_3$, measuring the rotating speed of the screw 8 and sensing back to a hydraulic proportional flow control valve $O_3$ controlled by control circuit 3, thus assuring a constant rotating speed of the hydraulic motor 10, irrespective of the changing torque resulting from introduction of the starch 4 recharge.

When the load time is completed, the screw 8 rotation is stopped and molding cycle Point D of FIG. 2 is reached. The time from molding cycle Points D to A of FIG. 2 allows for the starch 4 to plasticize completely under controlled temperature conditions as controlled by control circuit 1.

A temperature sensor circuit $I_1$ senses a thyristor heat regulator $O_1$ heating the extruder barrel 17 as directed by control circuit 1.

During the time interval from molding cycle Points B to E on FIG. 2, the mold 6 has cooled down sufficiently so that the finished capsule parts 7 can be ejected from the mold 6.

After ejection of the capsule parts 7, the work cycle returns to Point A of FIG. 2 where a certain volume of plasticized starch 14 has accumulated in front of the screw 8 (sensing circuit $I_4$ is actuated and time has elapsed) so that the work cycle of FIG. 2 can be repeated.

It is important to note the temperature and humidity control loops 5 and 6, for the maintenance of precise water content of the starch 4 in the hopper 5, which is essential for proper operation at the desired speeds.

The microprocessor 28 includes a memory section 51 to store the desired operating parameters; a sensing and signaling section 52 to receive the sensing signals of actual operating conditions, to detect the deviation between the desired and actual operating conditions, and to send signals for adjustment through the actuating section 53 to the thyristors and valves.

Figure 4:
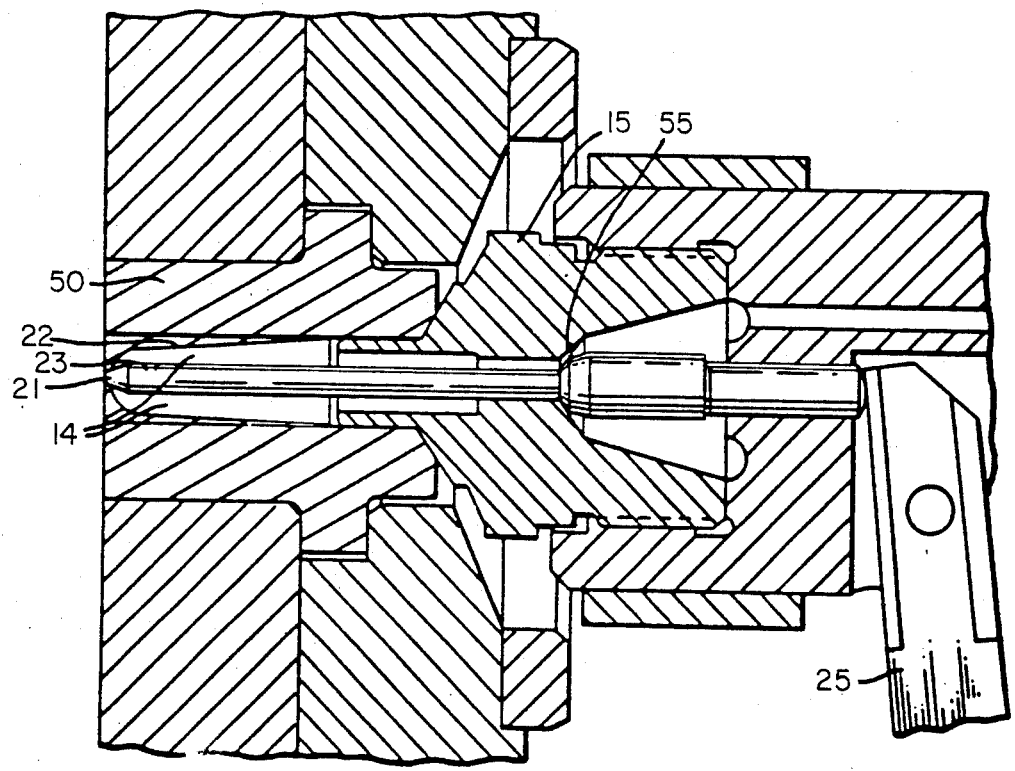
FIG. 4 is an expanded schematic of the exit end of the injection molding device.

Referring now to FIG. 4 there is shown the valve assembly 50 including the outlet port 21, the nozzle 22, the needle valve 23, and the bearing 15. These elements operate as follows:

At Point A in FIG. 2 the needle valve 23 is retracted from the outlet port 21 when the pressure in the starch 14 while the bearing 15 is pressed against the valve body so as to form an inlet opening 55 for plasticized starch 14 into the nozzle 22 which defines a charging chamber for plasticized starch 14. The plasticized starch 14 is injected through nozzle 22 and into the mold 6 during the mold-filling time between Points A and B in FIG. 2. At Point C in FIG. 2 the needle valve 23 is pushed forward so as to close the outlet port 21 during which time between Point C and E in FIG. 2, the inlet of mold 6 is closed and the capsule part 7 in the mold 6 is cooling. The needle valve 23 remains closed between Point E and A in FIG. 2 during which time the capsule part 7 is ejected from the mold 6.

The one-way valve 15 and the needle valve 23 are actuated by a spring-tensioned lever 25 which normally closes both the outlet port 21 and the nozzle 22 until the lever 25 is cam-actuated pursuant to signals from the microprocessor 28.

The thermomechanical properties of starch, i.e. storage and loss shear modules at different temperatures, are strongly dependent on its water content. The capsule molding process of the present invention can be used for starch with a water content preferably within a range of 5 to 30%. The lower limit is defined by the maximum processing temperature of 240° C., which in turn cannot be exceeded in order to avoid degradation. The upper limit is determined by the stickiness and distortion of the finished capsules. It should also be noted that plasticizing is caused by heat and pressure when dealing with thermoplastic materials; however, with starch it is necessary to also have strong shearing forces. The abbreviations in Table 2 below will be used hereinafter in this application:

TABLE 2

Abbreviations for Physical Parameters

| ABBREVIATION | UNIT | DESCRIPTION |
|---|---|---|
| $T_a, P_a$ | Degree C., $N \times m^{-2}$ | Ambient temperature and pressure. |
| H(T,P) | KJoule $\times$ Kg$^{-2}$ | Enthalpy of starch-water system at a temperature. |
| K(T,P) | $N^{-1} \times m^2$ | Compressibility of the starch at a given temperature and pressure. Its numerical value is the relative volume change due to change of pressure by a unit amount. |
| (T,P) | (Degree C.)$^{-1}$ | Volumetric thermal expansion coefficient of the starch at a given temperature and pressure. Its numerical value is the relative volume change due to change of temperature by a unit amount. |
| V(g,T,P) | Kg $\times$ sec$^{-1}$ | is the flow rate of the starch at a given temperature and shear deformation rate [sec.$^{-1}$] and pressure. Its numerical value is the volume of a melt leaving the exit cross-sectional area of an injection molding device in unit time due to the applied shear deformation rate. |
| $T_{G1}; T_{G2}$ | Deg C. | The temperature range of the glass-transition of the starch. |
| $T_{M1}; T_{M2}$ | Deg C. | The temperature range of the melting of the partially crystalline starch. |
| $T_M$ | | Melting temperature |
| $T_n(t)$ | Deg C. | The temperature of the starch in the nozzle area of the injection unit. |
| $T_r(t)$ | Deg C. | The temperature of the starch in the mold. |
| $P_t$ | $N \times m^{-2}$ | The pressure of the starch in the mold. |

TABLE 2-continued

| Abbreviations for Physical Parameters | | |
|---|---|---|
| ABBREVIATION | UNIT | DESCRIPTION |
| $P_n$ | $N \times m^{-2}$ | The pressure in the nozzle area of the starch. |
| X | | The water content of the starch, expressed as the weight fraction of the water-starch system. |

For the control and regulation of the injection molding process (IMP) we need knowledge of the (1) heat consumption of the melting process: $H(T_n, P_n) - H(T_a, P_a)$
(2) the heating rates of the starch in the injection molding device. To calculate this we need the heat conduction number of the starch and the heat transfer number of the starch and the specific material of construction of the barrel which is in contact with the starch. The heating rate and the heat consumption of the starch give the minimum time interval necessary to make the starch ready to inject and the necessary heating power of the injection molding device.
(3) the $T_n$ depends on X of the starch. If the water content of the starch in the mold is too low, the resulting $T_n$ will be too high and cause degradation. A minimum water content of 5% by weight is required to keep $T_n$ below 240° C.
(4) the flow rate V(g,T,P) is as well strongly dependent on the water content of the starch. To speed up the IMP we need a high flow rate V(g,T,P) which can be achieved by a higher water content.

The upper limit of the water content is defined by the stickiness and mechanical failure of the capsules; a water content of 0.30 cannot be generally exceeded.

The starch in the mold will reduce its volume due to the temperature change $T_t - T_a$. This would result in voids and diminution of size of the capsule, which therefore would be of unacceptable quality. It is an important requirement in capsule making that the dimensional deviations are less than 1%. To compensate for shrinking by the temperature change, the mold must be filled at a distinct pressure $P_n$. This filling pressure is determined by the quantities (T,P) and K(T,P). The injection pressure ($P_n$) depends again on $T_n$, which as was shown already is in turn strongly dependent on X.

Figure 5:
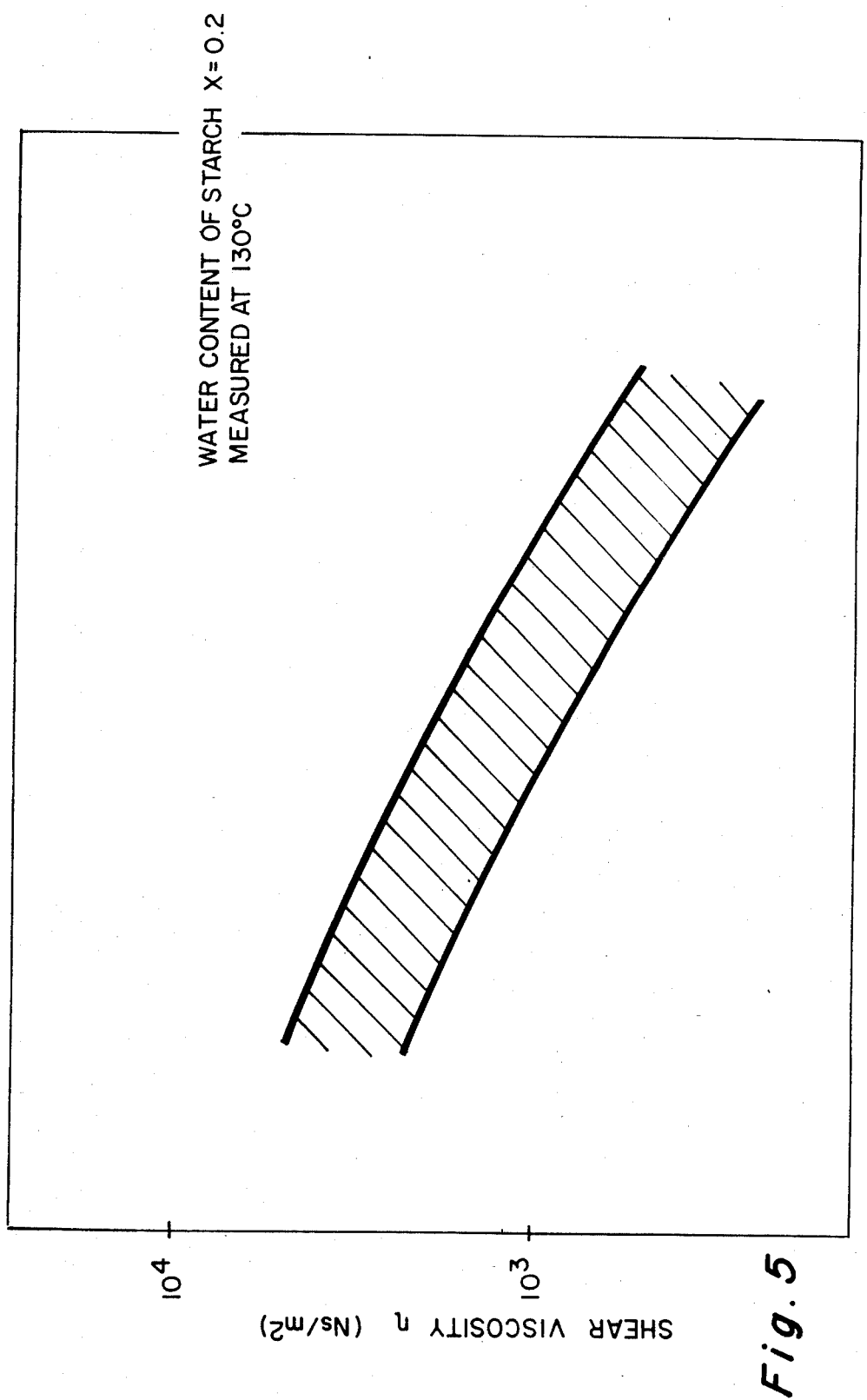
FIG. 5 is the diagram of dependence of shear viscosity of starch within the pertinent ranges of the shear rate in the present invention.

Referring now to FIG. 5, the shear rate dependent shear viscosity of starch at 130 degrees C. is shown for starch with a water content X of 0.2.

Figure 6:
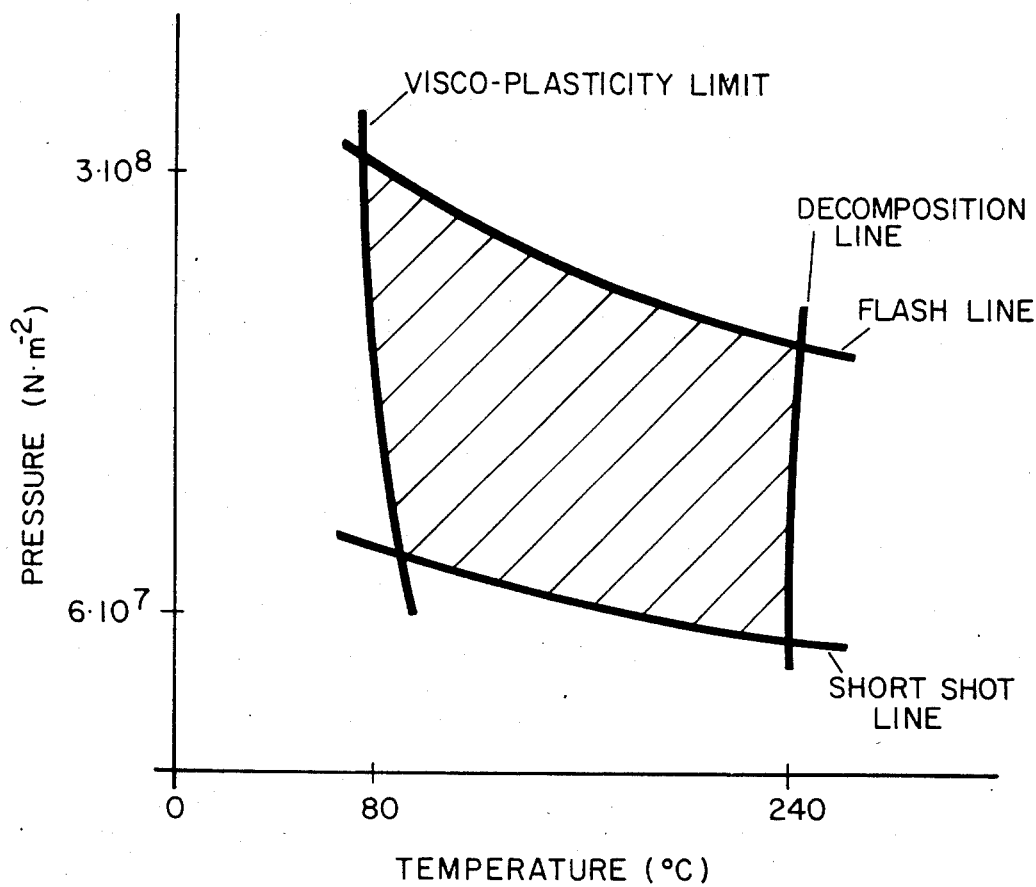
FIG. 6 is the diagram of molding area for starch within the ranges of temperature and pressure of starch for the present invention.

Referring now to FIG. 6, the molding area diagram for starch with water content of 0.24. During injection molding the plasticized starch is discontinuously extruded and immediately cooled in a mold of the desired shape of the capsule part. Moldability depends on the starch properties and the process conditions, of which the thermomechanical properties of the starch as well as the geometry and the temperature and pressure conditions of the mold are the most important. In the molding area diagram of FIG. 6 the limits of pressure and temperature are indicated for the processing of starch in the combined injection molder-microprocessor of the present invention. The maximum temperature of 240° C. is determined by visible degradation of the starch above that limit. The lower temperature limit of 80° C. was determined by the development of too high viscosity and melt elasticity in the preferred water content range X: 0.05 to 0.30. The higher pressure limits of $3 \times 10^8 N \times m^{-2}$ are given by the start of flashing when the melted starch flows in a gap between the various metal dies which make up the molds, thus creating thin webs attached to the molded starch capsule parts at the separating lines. The lower pressure limits of about $6 \times 10^7 N \times m^{-2}$ are determined by short shots, when the mold cannot be completely filled by the starch. Shown below in Table 3 are the working parameters for the injection molding process using the starch composition of the present invention.

TABLE 3

| WORKING PARAMETERS FOR INJECTION MOLDING PROCESS | |
|---|---|
| Density | $1.5- \times 10^3$ kg $\times$ m$^{-3}$ |
| Cristallinity | 20 to 70% |
| $H(T_n,P_n)-H(T_a,P_a)$ | 63 KJoule $\times$ kg$^{-1}$ |
| Net heating performance for 10 kgs. melt/h (corresponding to $10^6$ capsules/h) | $6.3 \times 10^2$ KJoule |
| $(T_a,P_a)$ | $3.1 \times 10^{-4}$ (Degree° C.)$^{-1}$ |
| Contraction due to crystallization | negligible |
| Critical shear deformation rate | $10^4$-$10^6$ sec$^{-1}$ |

Figure 7:
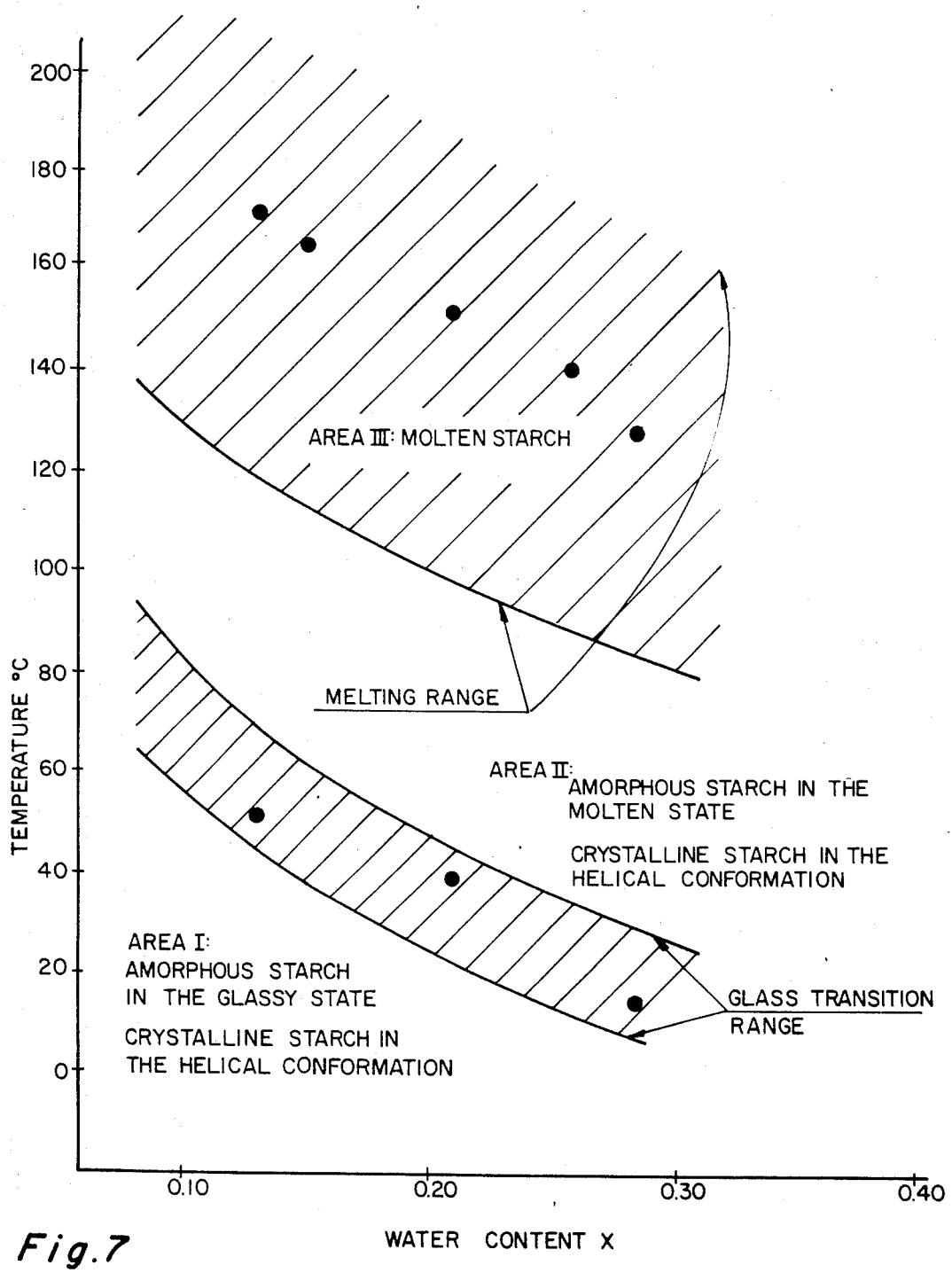
FIG. 7 is the diagram of dependence of glass transition temperature range and melting temperature range for the pertinent water content ranges of starch.

The starch compositions of the present invention are extruded and molded as described below:

Referring now to FIG. 7 the glass transition range and the melting temperature range is shown as a function of the composition of the starch-water system. The melting range is very broad with over 100° C. in comparison with the melting range of e.g. gelatin, which comes to about 20° C. At temperatures below the glass transition range, ordinary starch, as available commercially, is a partially crystalline polymer containing approximately 30-100% amorphous and approximately 0-70% crystalline parts by volume.

By raising the temperature of said starch at a distinct water content the starch passes through the glass transition range.

Figure 8:
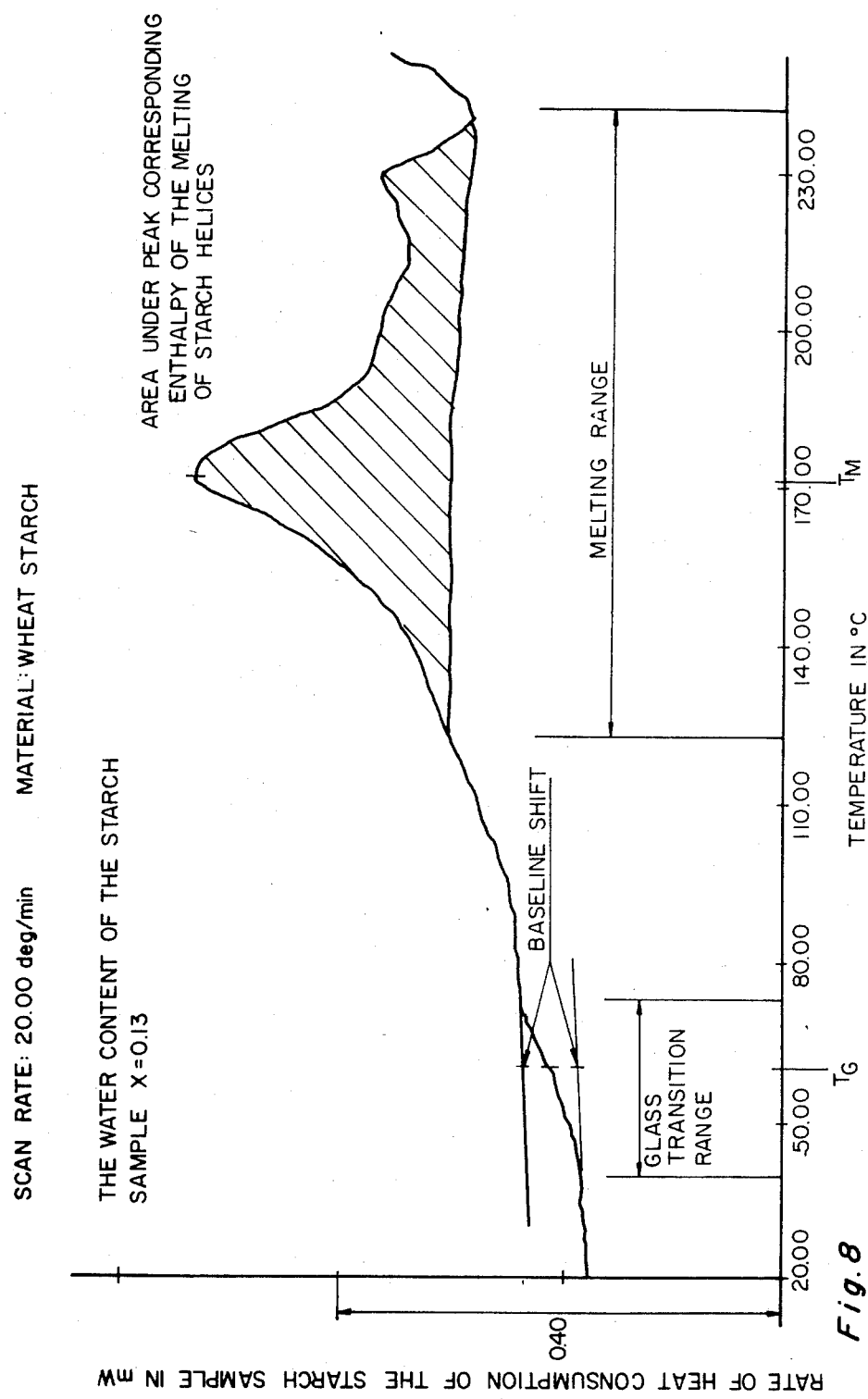
FIG. 8 is the diagram of dependence of differential calorimeter scan in which the heat consumption rate of the starch is plotted for the pertinent temperature range of the present invention.

Referring again to FIG. 1 said heating process of the starch will take place within the extruder barrel 17. Referring again to FIG. 2 said heating process of the starch will take place during the entire injection molding work cycle. The area in FIG. 7 between the glass transition range and the melting range is called area II. In area II we find crystalline starch and a starch melt. The glass-transition is not a thermodynamic transition range of any order but is characterized by a change of the molecular movement of the starch molecules and by a change of the bulk storage module of the amorphous starch by several orders of magnitude. By passing from area II to area I in FIG. 7 the translational movements of the starch molecules of those of large parts of said molecules will be frozen in the glass transition temperature range and this is reflected by a change in the specific heat ($c_p$) and the volumetric thermal expansion coefficient ($\alpha$) in said temperature range. By passing from area II to area III due to crossing the melting range of the crystalline starch the helically ordered part of the starch will melt. Referring to FIG. 1 said heating process of the starch will take place within the extruder barrel 17. Referring again to FIG. 2, said heating process of the starch will take place during the entire injection molding work cycle. Said helix-coil transition is a true thermodynamic transition of the first order and is an endothermic process. Said transitions can be detected by scanning calorimetry or by measurement of the change of the linear viscosity bulk storage module due to change of the temperature. A typical plot of a temperature scan with a differential calorimeter is shown in FIG. 8. On the ordinate is plotted the velocity of the heat consumed by the sample relative to a reference (empty sample holder). The velocity of heat consumption of the sample is due to the change of the temperature of the starch sample, and said temperature is plotted on the abscissa as degrees of Celsius. The base line shift on said plot is corresponding to the glass transition and the peak to the melting or to the helix-coil transition. The linear viscoelastic bulk storage module E can be measured at small sinusoidal shear deformations of the starch sample.

Figure 9:
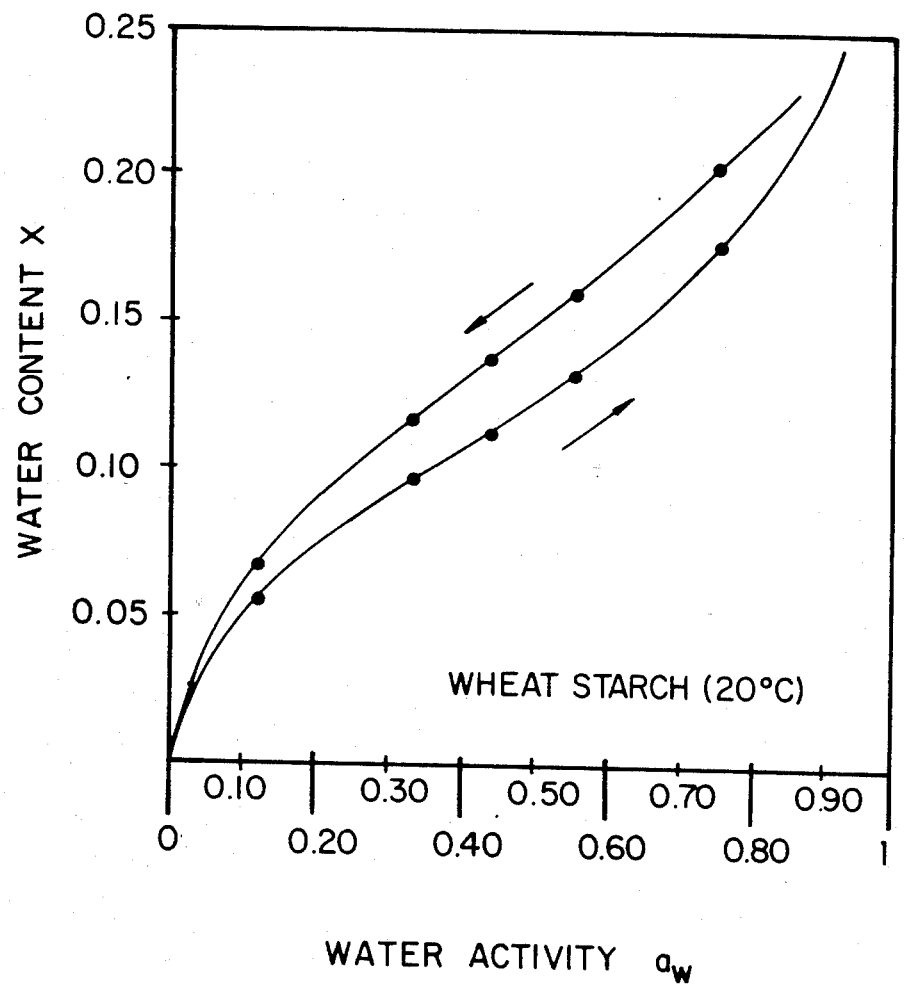
FIG. 9 is a diagram of dependence of equilibrium water content of the starch in the water activity program.

Referring again to FIG. 1 the heating of the starch 4 to a temperature higher than $T_M$ takes place in the forward part of the extruder barrel 17. Said heating process will be maintained not only by the heating coils 18 but to an important proportion by the internal friction during the screw rotation and the injection process due to the high deformational rates. It was found that the reversible elastic deformation of the injection molded starch 14 after opening the mold 6 is negligible if the temperature of the plasticized starch 14 during the injection process is higher than $T_M$, otherwise the molding sequence would drop by at least an order of magnitude.

area of the extruder barrel, it is necessary to work at an injected sequence which is short. To establish a constant and high enough water content of the starch in the extruder barrel, it is further necessary to use starch with the proper shape of the sorption isotherm. (See FIG. 9). The constant water content of the starch in the extruder barrel is necesary due to the maintenance of constant production conditions. The water content of the starch during the injection must fulfill the condition: X higher than 0.05 otherwise $T_M$ is also higher than 240° C. and this is undesirable due to degradation of the starch.

In the procedure of branching and crosslinking of starch, it is important to add crosslinking agents, especially the covalent crosslinking agents, shortly before injection of the molten starch.

Referring again to FIG. 1, an aqueous solution of crosslinking agents is injected in front of a mixing system being placed between barrel 17 and nozzle 15. Referring now to FIG. 4, this device is integrated in the valve body 50. For example, the crosslinking reaction mainly occurs during the injection cycle and the time after ejection of the capsule. By the above described technology on branching and crosslinking there is no disadvantage of changing the thermo-mechanical properties of the starch polymers during the melting and solution process.

The starch compositions are extruded and injected under the following conditions given in Table 4 below:

TABLE 4

| Injection and Molding Conditions for Starch | | | | | |
|---|---|---|---|---|---|
| Injection Unit | | | | | |
| Screw diameter mm | | 24 | 28 | 32 | 18 |
| Injection pressure N × m$^{-2}$ | | 2.2 × 10$^8$ | 1.6 × 10$^8$ | 1. × 10$^8$ | |
| Calcuted injection cm$^3$ | | 38 | 51.7 | 67. | 21.3 |
| Effective screw length L:D | | 18.8 | 16.1 | 13. | 18 |
| Plasticising capacity (PS) kg/h(max.) | 1a) | 13.5 | 21.2 | 21. | |
| | 11a) | 9.2 | 14.5 | 15 | |
| | 1b) | 23.6 | 34 | 36 | |
| | 11b) | 17.5 | 27 | 27. | |
| Screw stroke mm(max.) | | 84 | 84 | 84 | 84 |
| Injection capacity kW | | 30 | 30 | 30 | |
| Injection velocity mm/s(max.) | | 2000 | 2000 | 2000 | 2000 |
| Nozzle contact force kN | | 41.2 | 41.2 | 41.2 | 41.2 |
| Screw rotating speed min$^{-1}$ | Var. 1a) | | 20 | −80 | |
| | 11a) | | 20 | −17 | |
| | Var. 1b) | | 20 | −60 | |
| | 11b) | | 20 | −40 | |
| Number of heating zones | | 5 | 5 | 5 | 5 |
| Installed heating capacity kW | | 6.1 | 6.1 | 6. | |
| Molding unit | | | | | |
| Clamping force kN | | | | 60 | |

Referring again to FIG. 2 the necessary cooling period for the plasticized starh in the molds to prevent any reversible elastic deformation of said starch will take place between points B and E of the working cycle. A restriction of the molding sequence to low speed coupled with long keeping of the starch in the mold is undesirable because of two reasons: low output of the product and loss of water content of the starch in the extruder. At the elevated injection temperature there is always a transport of water from the hot to the cold starch in the extruder barrel. Said water transport can be compensated due to the transport of the starch by the screw in the opposite direction.

Referring again to FIG. 1 said transport of starch 4 will be maintained by screw 8. Referring again to FIG. 2 said transport of starch will take place between the points C and D of the working cycle. To build up a stationary water content of the starch in the melting While the preferred embodiment of the injection molding apparatus is for the method of producing starch capsules from various types of starch, it has been found that quality capsules may also be manufactured utilizing the present invention with starch modified by (a) crosslinking agents as: epichlorohydrin, anhydride of dicarboxylic acid, formaldehyde, phosphorus oxychlorine, metaphospate, acrolein, organic divinylsulfons and the like.

(b) crosslinking the starch with microwaves and the like.

(c) prior processing like treatment with acids and/or enzymes in order to yield dextrines and/or pregelatinizing and/or treatment with ultrasonic and/or treatment with gamma radiation.

(d) Chemical derivatives as: oxydized starch, starch monophosphate, starch diphosphate, starch acetate, starch sulfate, starch hydroxyethylether, carboxymethyl starch, starch ether, 2-hydroxypropyl starch, alphatized starch, starch xanthide, starch chloroacetic acid, starch ester, formaldehyde starch, sodium carboxymethyl starch; and (e) mixtures or combinations of these modified starches and starch modification procedures (a) to (d) respectively.

In addition it has been found that the injection molding apparatus of the present invention can produce quality capsules with various types of starch and/or with the above mentioned modified starches (a), (b), (c), (d) and (e) combined with extenders such as sunflower proteins, soybean proteins, cotton seed proteins, peanut proteins, blood proteins, egg proteins, rape seed proteins and acetylated derivatives thereof, gelatin, crosslinked gelatin, vinylacetate, polysaccharides as cellulose, methylcellulose, hydroxypropyl cellulose, hydroxypropyl-methylcellulose, hydroxymethyl-cellulose, hydroxyethylcellulose, sodium carboxy methylcellulose, polyvinyl-pyrrolidone, bentonite, agar-agar, gum arabic, guar, dextran, chitin, polymaltose, polyfructose, pectin, alginates, alginic acids and the like, monosaccharides as glucose, fructose, saccharose and the like, oligosaccharides as lactose and the like, silicates, carbonates and bicarbonates, the quantity of extender is controlled so as not to effect the ability of the starch to be injection molded. In addition it has been found that the injection molding apparatus of the present invention can produce capsules having enteric properties (2 hours resistant in gastric juice, well soluble within 30 minutes in intestinal juice according to USP XX) with various types of starch and/or with the above mentioned modified starches (a), (b), (c), (d) and (e) combined with enteric polymers as hydroxypropyl-methylcellulose phtalate (HPMCP), cellulose acetylphtalate (CAP), acrylates and methacrylates, polyvinyl-acetate-phtalate (PVAP), phtalated gelatin, succinated gelatin, crotonic acid, shellac and the like. The quantity of extender is controlled so as not to effect the ability of the starch to be injection molded.

For the manufacturing of capsules with different types of starches and/or modified starches and/or extended starches as mentioned above, the utilization of plasticizers, lubricants and coloring agents specifically of pharmaceutical grades leads to optimal product qualities:

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2-propylenglycol, mono-, di-, tri-acetates of glycerol etc. are utilized at various concentrations of about 0.5-40% preferably at 0.5-10% based upon the weight of the starch composition.

Pharmacologically acceptable lubricant, such as lipids, i.e. glycerides (oils and fats), wax and phospholipids, such as unsaturated and saturated plant fatty acids and salts thereof, such as the stearates of aluminum, calcium, magnesium and tin; as well as talc, silicones, etc. are to be used at concentrations of about 0.001-10% based upon the weight of the starch composition.

Pharmaceutically acceptable coloring agents, such as azo-dyes and other dyestuffs and pigments as iron oxides, titanium dioxides, natural dyes etc. are used at concentrations of about 0.001-10% preferably at 0.001-5% based upon the weight of the starch composition.

EXAMPLES

To test the method and apparatus as described before according to the present invention, batches of commercially available native starch with different water contents and extenders were prepared and conditioned and then tested in an injection molding machine at different working conditions.

Referring to FIG. 2 the cycle times of the injection molding-microprocessor apparatus are as follows:

| Cycle Points | Times |
| --- | --- |
| A-B | 1 second, variable, depending on temperature |
| B-C | 1 second |
| C-D | 1 second |
| D-E | Variable depending on temperature |
| E-A | 1 second |

Pressure in the nozzle: $2 \times 10^8 N \times m^{-2}$. Temperatures at different points of screw: (variable, see Examples below.)

In the following Examples the abbreviations mean:
$T_b$: temperature at beginning of screw (°C.)
$T_m$: temperature at middle of screw (°C.)
$T_e$: temperature at end of screw (°C.)
$T_n$: temperature at nozzle (°C.)
LFV: linear flow velocity (mm/second)
L: flow length (cm.)
D: film thickness (cm.)

Acceptable starch capsules were processed according to the starch compositions and to the working conditions tabulated in the Examples below:

EXAMPLE 1

Starch composition:
Wheat starch, gelatin 150B, water: 8.2% bw, 73.8 bw, 18 bw. Working conditions:

| number | $T_b$ | $T_m$ | $T_e$ | $T_n$ | L/D | LFV |
| --- | --- | --- | --- | --- | --- | --- |
| 765 | 125 | 130 | 140 | 140 | 66 | 1000 |

EXAMPLE 2

Starch composition:
Wheat starch, gelatin 150B, water: 41% bw, 41% bw, 18% bw.
Working conditions:

| number | $T_b$ | $T_m$ | $T_e$ | $T_n$ | L/D | LFV |
| --- | --- | --- | --- | --- | --- | --- |
| 126S | 125 | 135 | 140 | 140 | 66 | 820 |

EXAMPLE 3

Starch composition:
Wheat starch, gelatin 150B, water: 67.6% bw, 24.6% bw, 158% bw.
Working conditions:

| number | $T_b$ | $T_m$ | $T_e$ | $T_n$ | $\frac{L}{D}$ | LFV |
|---|---|---|---|---|---|---|
| 298S | 125 | 135 | 140 | 140 | 66 | 1200 |

EXAMPLE 4

Starch compositions:
Wheat starch, water: 79.4% bw, 20.6% bw.
Working conditions:

| number | $T_b$ | $T_m$ | $T_e$ | $T_n$ | $\frac{L}{D}$ | LFV |
|---|---|---|---|---|---|---|
| 305S | 115 | 130 | 140 | 140 | 66 | 820 |

EXAMPLE 5

Starch composition:
Wheat starch, water, erythrosine: 78.32%, 21.6% bw, 0.0078% bw.
Working conditions:

| number | $T_b$ | $T_m$ | $T_e$ | $T_n$ | $\frac{L}{D}$ | LFV |
|---|---|---|---|---|---|---|
| 349S | 110 | 125 | 135 | 135 | 66 | 1000 |

EXAMPLE 6

Starch composition:
WHeat starch, HPCMP, lubricants+plasticizers, water: 9.2% bw, 74.1% bw, 5.1% bw, 7.5% bw.
Working conditions:

| number | $T_b$ | $T_m$ | $T_e$ | $T_n$ | $\frac{L}{D}$ | LFV |
|---|---|---|---|---|---|---|
| 349S | 110 | 125 | 135 | 135 | 66 | 1000 |

This starch composition yielded an enteric capsule.

EXAMPLE 7

Starch composition:
Wheat starch, water: 78.5% bw, 21.5% bw.
Working conditions:

| number | $T_b$ | $T_m$ | $T_e$ | $T_n$ | $\frac{L}{D}$ | LFV |
|---|---|---|---|---|---|---|
| 400S | 130 | 150 | 160 | 160 | 66 | 820 |
| 404S | 110 | 115 | 125 | 125 | 66 | 820 |

EXAMPLE 8

Starch composition:
Wheat starch, water: 87.3% bw, 12.7% bw.
Working conditions:

| number | $T_b$ | $T_m$ | $T_e$ | $T_n$ | $\frac{L}{D}$ | LFV |
|---|---|---|---|---|---|---|
| 405S | 150 | 160 | 170 | 170 | 66 | 820 |

EXAMPLE 9

Starch composition:
Wheat starch, Calcium-stearate, water: 76.8% bw, 3% bw, 20.2% bw.
Working conditions:

| number | $T_b$ | $T_m$ | $T_e$ | $T_n$ | $\frac{L}{D}$ | LFV |
|---|---|---|---|---|---|---|
| 411S | 100 | 110 | 135 | 135 | 66 | 880 |
| 413S | 130 | 140 | 160 | 160 | 66 | 820 |

EXAMPLE 10

Starch composition:
Wheat starch, glycerine, water: 77.2% bw, 3% bw, 19.8% bw.
Working conditions:

| number | $T_b$ | $T_m$ | $T_e$ | $T_n$ | $\frac{L}{D}$ | LFV |
|---|---|---|---|---|---|---|
| 410S | 100 | 110 | 130 | 130 | 66 | 860 |
| 414S | 130 | 140 | 160 | 160 | 66 | 840 |

EXAMPLE 11

Starch composition:
Wheat starch, Polyethylene-glycol (10,000 m.w.), water, talcum: 72.5% bw, 3% bw, 22.5% bw, 2% bw.
Working conditions:

| number | $T_b$ | $T_m$ | $T_e$ | $T_n$ | $\frac{L}{D}$ | LFV |
|---|---|---|---|---|---|---|
| 412S | 100 | 110 | 130 | 130 | 66 | 840 |
| 415S | 130 | 140 | 160 | 160 | 66 | 840 |

EXAMPLE 12

Starch composition:
Potato starch, water: 80.7% bw, 19.3% bw.
Working conditions:

| number | $T_b$ | $T_m$ | $T_e$ | $T_n$ | $\frac{L}{D}$ | LFV |
|---|---|---|---|---|---|---|
| 417S | 100 | 110 | 130 | 130 | 66 | 840 |

EXAMPLE 13

This example demonstrated the dependence of the capsules disintegration properties on the content of amylose. For these tests, the capsules were filled with lactose.

| starch composition | working conditions (°C.) $T_b, T_m, T_e, T_n, \frac{L}{D}$ LFV | disintegration property of the capsules |
|---|---|---|
| maize starch (about 20% amylose) | 110, 120, 140, 140, 66, 840 | flocculation in water of 36° C., disintegration within 30 minutes |
| maize starch (65% amylose) 80% b.w., water 20% b.w. | 110, 120, 140, 140, 66, 840 | no opening in water of 36° C. within 30 minutes |

-continued

| starch composition | working conditions (°C.) $T_b$, $T_m$, $T_c$, $T_n$, $\frac{L}{D}$ LFV | disintegration property of the capsules |
|---|---|---|
| maize starch (0% amylose, 100% amylopectin) 79.2 b.w., water 20.8% b.w. | 110, 120, 140, 140, 66, 836 | disintegration in water of 36° C., disintegration within 30 minutes |

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

What is claimed is:

1. A process for forming starch into an article using an injection molding technique which process comprises:
    (A) maintaining a starch/water composition at a water content between 5-30% by weight of the composition under controlled conditions of temperature and pressure,
    (b) heating said starch/water composition at elevated pressure above its glass transition temperature and melting point while maintaining said water content, to form a melt,
    (c) further heating and plasticizing said molten starch/water composition to dissolve the starch in the water to form an essentially molecularly dispersed solution of the melt,
    (d) injecting the starch/water melt into a mold cavity while maintaining said predetermined water content,
    (e) cooling the composition in the mold to form a molded product at a temperature below the glass transition temperature of said composition and,
    (f) ejecting the molded product from said mold.

2. A process according to claim 1 wherein the elevated temperatures in each step is in the range from 80° to 240° C.

3. A process according to claim 1 or 2 wherein the elevated pressure is in the range from $600 \times 10^5$ to $30000 \times 10^5$ Newton/square meter.

4. A process according to claim 1, 2 or 3 wherein the starch is derived from a corn, wheat, potato, rice or tapioca starch or a mixture thereof.

5. A process according to any one of claims 1 to 4 wherein the native starch is mixed with at least one number of a class consisting of an extenders, a plasticizers, a lubricants and coloring agents.

6. A process according to claim 1 wherein a plasticizer is present in an amount of from 0.5 to 40% based upon the weight of the starch.

7. A process according to claim 1 wherein a lubricant is present in an amount of 0.001 to 10% based on the weight of the starch.

8. A process according to claim 1 or 6 wherein a coloring agent is present in an amount of from 0.001% to 10% based on the weight of the starch.

9. A process according to claim 1 wherein an extender is added and chosen from sunflower proteins, soybean proteins, cotton seed proteins, peanut proteins, blood proteins, egg proteins, rape seed proteins and acetylated derivatives thereof; gelatin, crosslinked gelatin, vinylacetate, polysaccharides such as cellulose, methylcellulose, hydroxypropyl-cellulose, hydroxypropylmethylcellulose, hydroxymethyl-cellulose, hydroxyethylcellulose, sodium carboxy methylcellulose, polyvinylpyrrolidone, agar-agar, gum arabic, guar, dextran, chitin, polymaltose, polyfructose, pectin, alginates, alginic acids, monosaccharides preferably glucose, fructose, saccharose; and oligosaccharides lactose, bentonite, silicates, carbonates and bicarbonates.

10. A process according to claim 6 wherein the plasticizer is chosen from: polyethylene glycol and low molecular weight organic plasticizers, including glycerol, sorbitol, dictylsodium sulphosuccinate, triethyl citrate, tributyl citrate, 1,2 propyleneglycol, mono-, di-, and tri-acetates of glycerol.

11. A process according to claim 7 wherein the lubricant is chosen from: lipids; unsaturated and saturated plant fatty acids and salts thereof; stearates of aluminum, calcium, magnesium and tin; talc and silicones.

12. A process according to claim 11 wherein the lubricant is a glyceride, a phospholipide or a mixture thereof in an amount of from 0.001-10% by weight of the starch.

13. A process according to any one of claims 1, 2, 3, 4, 6, 7, or 9 wherein the starch is mixed with one or more polymer having enteric properties and being chosen from: hydroxypropylmethylcellulosephthalate (HPMCP), cellulose-acetylphthalate (CAP), acrylates and methacrylates, polyvinylacetatephthalate (PVAP), phthalated gelatin, succinated geltin, crotonic acid, and shellac.

14. An injection molded article made according to the process of claims 1, 2, 3, 4, 6, 7 or 9.

15. A capsule whenever produced by a process as claimed in any one of claims 1, 2, 3, 4, 6, 7 or 9.

16. A starch/water composition characterized in that said composition is obtained by
    (a) maintaining a starch/water composition at a water content of 5-30% by weight of the composition under controlled conditions of temperature and pressure,
    (b) heating said starch/water composition under pressure above its glass transition temperature and melting point while maintaining said water content, to form a melt,
    (c) further heating and plasticizing said molten starch/water composition to dissolve the starch in the water to form melt as a molecularly dispersed solution of said melt.

17. A composition according to claim 16 characterized in that said composition is held at a temperature of 80°-240° C.

18. A composition according to claim 17 characterized in that said composition is held at a pressure of $600 \times 10^5$ to $3000 \times 10^5$ N/M².

19. A molded article formed from a composition according to any one of the claims 16, 17 or 18.

20. A self-sustaining molded article made from starch having a microstructure formed by heating a starch-water mixture wherein the water content is between 5 and 30% by weight beyond the glass transition and melting temperatures of starch to form a melt as a molecularly dispersed solution and cooling said melt to minimize shrinkage.

21. A composition according to claim 17 wherein the temperature is greater than 100° C.

22. A composition according to claim 16 wherein the water content is between 15 and 22%.

23. A composition according to claim 16 wherein the water content is between 15 and 19%.

24. A process according to claim 6 wherein plasticizer is present from 0.5–10% by weight.

* * * * *